(12) United States Patent
Boll et al.

(10) Patent No.: US 8,252,924 B2
(45) Date of Patent: Aug. 28, 2012

(54) PROCESS FOR PREPARING BENZOMORPHOLINE DERIVATIVES BY HYDROGENATING O-NITROPHENOXY CARBONYL COMPOUNDS

(75) Inventors: Matthias Boll, Köln (DE); Burkhard Koch, Köln (DE)

(73) Assignee: SALTIGO GmbH, Langenfeld, DE (US)

( * ) Notice: Subject to any disclaimer, the term of this patent is extended or adjusted under 35 U.S.C. 154(b) by 85 days.

(21) Appl. No.: 12/641,426

(22) Filed: Dec. 18, 2009

(65) Prior Publication Data
US 2011/0040089 A1  Feb. 17, 2011

(30) Foreign Application Priority Data
Dec. 23, 2008 (DE) .......... 10 2008 062 906

(51) Int. Cl.
*C07D 265/30* (2006.01)
*C07D 295/00* (2006.01)

(52) U.S. Cl. .......... 544/105; 544/59

(58) Field of Classification Search .......... 544/105
See application file for complete search history.

(56) References Cited

U.S. PATENT DOCUMENTS

| | | | |
|---|---|---|---|
| 2,381,935 A * | 8/1945 | Strain et al. .......... 544/105 |
| 4,623,650 A | 11/1986 | Gilligan et al. |
| 4,638,067 A | 1/1987 | Culbertson et al. |
| 6,395,403 B2 * | 5/2002 | Schmidt .......... 428/570 |
| 2004/0044206 A1 | 3/2004 | Munson et al. |
| 2006/0017946 A1 | 1/2006 | Peiro |

FOREIGN PATENT DOCUMENTS

| | | |
|---|---|---|
| CN | 1861253 | 11/2006 |
| WO | WO 0190088 A1 * | 11/2001 |
| WO | 2006118923 | 11/2006 |

OTHER PUBLICATIONS

S. Nishimura, Handbook of Heterogeneous Catalytic Hydrogenation for Organic Synthesis 1-63, 315-386 (2001).*
Bhaumik; (Canadian Journal of Chemistry (2003), 81(3), 197-198).
Han et al.; (Tetrahedron Letters (1985), 26(50), 6233-4).
Santra et al.; (Journal of Molecular Catalysis (1987), 39(3), 279-92).
Lu, et al. (Zhejiang Gongye Daxue Xuebao (2002), 30(5), 464-466.
European Search Report from co-pending Application EP09178883 dated Feb. 26, 2010, 2 pages.

* cited by examiner

*Primary Examiner* — James O Wilson
*Assistant Examiner* — Alexander R Pagano
(74) *Attorney, Agent, or Firm* — Michael A. Miller

(57) ABSTRACT

A process for preparing benzomorpholine derivatives is described, in which an o-nitrophenoxy carbonyl compound is hydrogenated in the presence of extraneous metal-doped sponge metal catalysts based on nickel or cobalt with ring formation.

10 Claims, 2 Drawing Sheets

Fig. 1: Diagram for Example 3
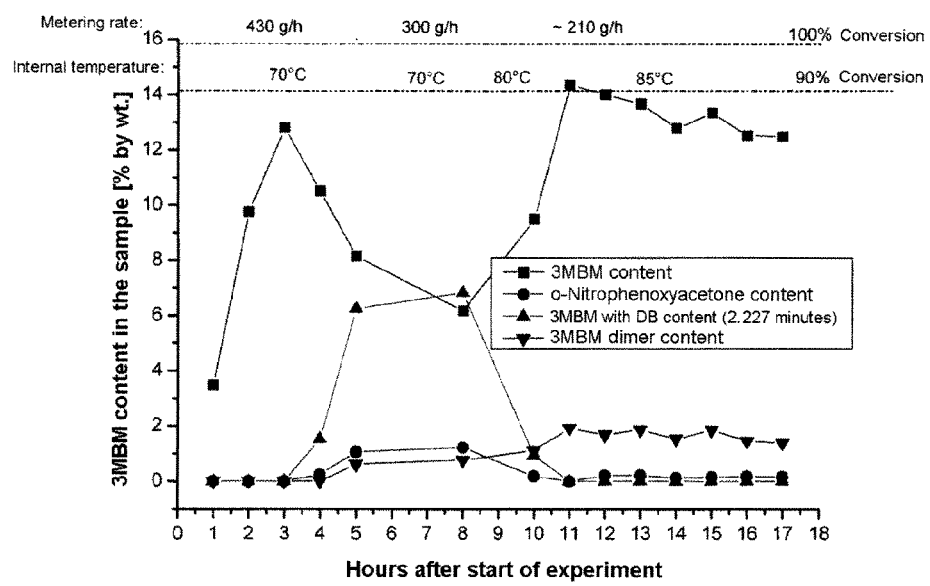
Fig. 2: Diagram for Example 4
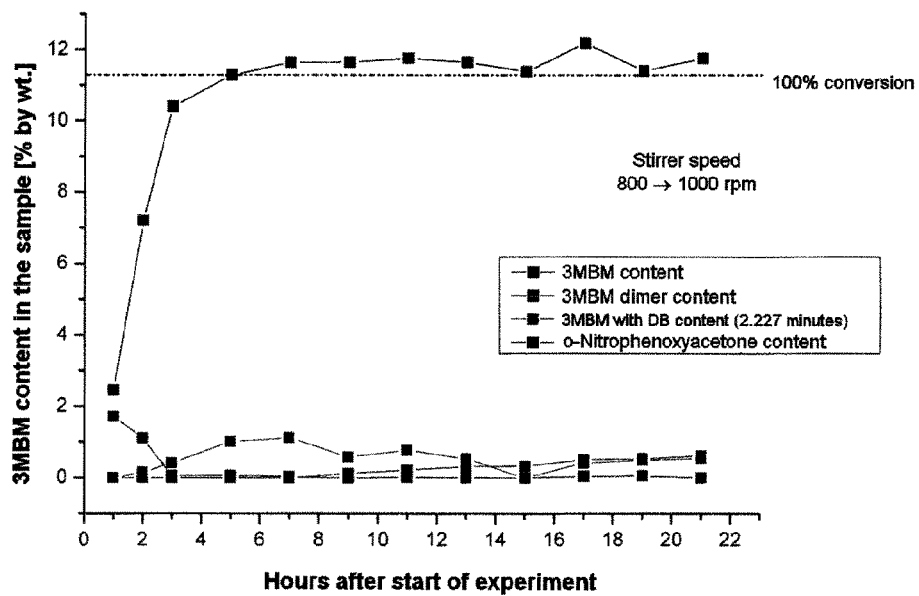

Fig. 3: Diagram for Example 10
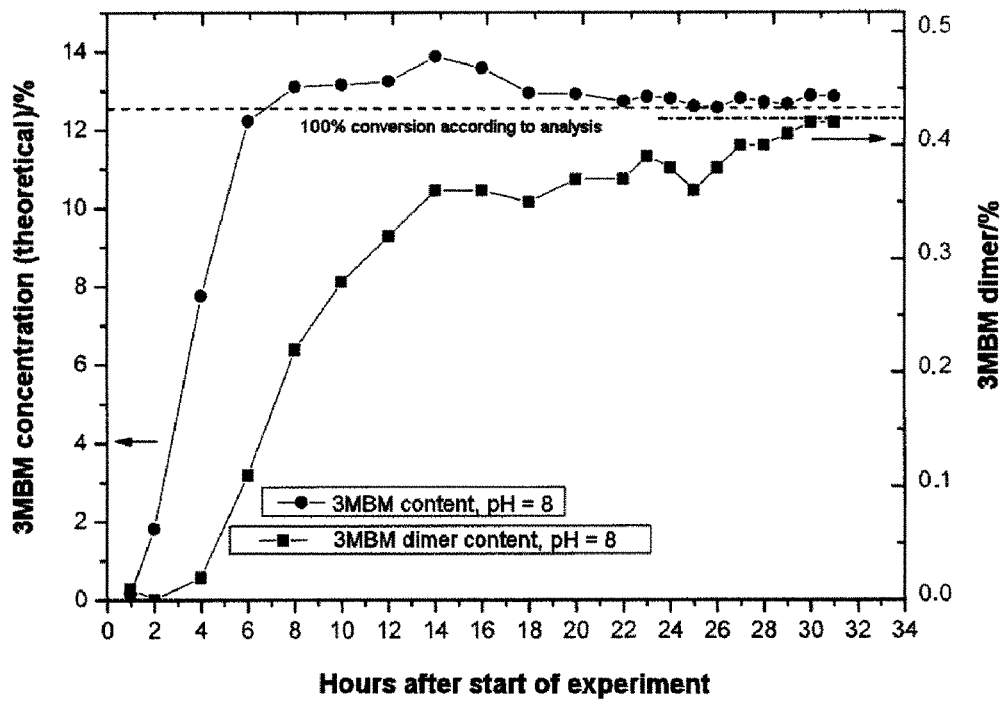
Fig. 4: Diagram for Example 11
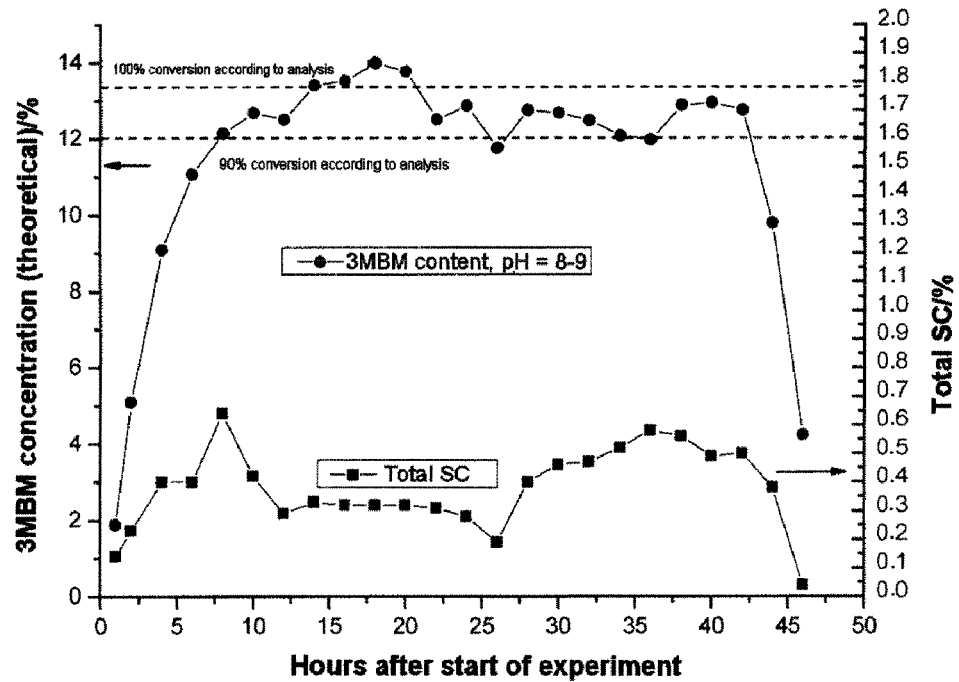

PROCESS FOR PREPARING BENZOMORPHOLINE DERIVATIVES BY HYDROGENATING O-NITROPHENOXY CARBONYL COMPOUNDS

The invention relates to a process for preparing benzomorpholine derivatives, in which an o-nitrophenoxy carbonyl compound is hydrogenated in the presence of extraneous metal-doped sponge metal catalysts based on nickel or cobalt with ring formation.

The hydrogenation of ortho-nitrophenoxyacetone (oNPA) to 3-methylbenzomorpholine (3MBM) is a commercially used chemical reaction with hydrogen under pressure in the presence of a catalyst. The reaction is catalysed on the industrial scale by noble metal catalysts, here in particular platinum catalysts on activated carbon.

3-Methylbenzomorpholine (3MBM) is an industrially prepared intermediate for the production of dyes and in the crop protection industry. 3-MBM is currently prepared by the conversion under moderate hydrogen pressure over a noble metal catalyst. Disadvantages of this process are the short service lives of the catalyst, the batchwise method specified and the comparatively long hydrogenation times coupled with simultaneously high costs for the noble metal-containing catalyst. In addition, a series of by-products are formed, which reduce the yield and purity of the product. This process is described in US 2006/0017946A1.

Instead of the expensive noble metal catalysts, it is in principle also possible to use so-called sponge metal catalysts (also known as skeletal catalysts) based on nickel, as described in U.S. Pat. No. 2,381,935 with an example. Such a catalyst is prepared by leaching an aluminium-nickel alloy with, for example, sodium hydroxide solution. In that document, a 56% by weight solution of oNPA in methanol was hydrogenated under comparatively severe conditions at 120° C.-170° C. with a Raney nickel catalyst which is not described in detail. About 20 g of oNPA per g of catalyst were converted in the example cited.

The reduction of aromatic nitro groups with hydrogen to the corresponding amines as an intermediate (which is not isolated and is only suspected in the present reaction) is performed globally on the industrial scale in the chemical industry. In principle, a whole series of catalysts are suitable for nitro reductions, starting from nickel or cobalt catalysts (in the form of the corresponding "sponge metal catalysts" or else in fine distribution on support materials). Mixtures of nickel and other metals, for example iron, molybdenum, chromium (all likewise referred to as "sponge metal catalysts") are likewise suitable in principle. Such catalysts are prepared by leaching an aluminium-containing metal alloy which contains the corresponding elements, generally with alkali metal hydroxide solution at elevated temperatures. These alloys can also be used for nitro reduction at low temperature in aqueous phase with addition of ammonium chloride, as reported by Bhaumik (Canadian Journal of Chemistry (2003), 81(3), 197-198).

In addition to these comparatively cost-effective catalyst types, noble metal catalysts on support materials are also useful for the nitro reduction, for example platinum or palladium on activated carbon, the reactivity of which, like that of the sponge metal catalysts, can also be attenuated in a controlled manner with the addition of ammonia or another amine or another catalyst poison. These catalysts have two disadvantages compared to the sponge metal catalysts based on nickel or cobalt; firstly, they are generally more difficult to filter and the associated catalyst losses are greater; secondly, the purchasing and recycling costs for noble metal catalysts are generally significantly higher.

For these reasons, sponge metal catalysts are generally used very frequently in industry.

BRIEF DESCRIPTION OF THE DRAWINGS

FIG. 1 illustrates the yield of 3MBM according to Example 3.

FIG. 2 illustrates the yield of 3MBM according to Example 4.

FIG. 3 illustrates the yield of 3MBM according to Example 10.

FIG. 4 illustrates the yield of 3MBM according to Example 11.

DETAILED DESCRIPTION OF THE INVENTION

Other means of reducing nitro groups, for instance the reduction with zinc, tin or iron in HCl proposed in Organikum (21$^{st}$ edition, p. 627 ff., Wiley VCH, Weinheim), play just as minor a role in the chemical industry as the reduction with, for example, hydrazine, as described, inter alia, by Han et al. (Tetrahedron Letters (1985), 26(50), 6233-4). Homogeneous catalysts based on noble metals have also already been mentioned for the reduction, for example by Sandra et al. (Journal of Molecular Catalysis (1987), 39(3), 279-92). In the examples specified above, moreover, only the nitro group on the aromatic was always hydrogenated; a further, intramolecular reductive amination as suspected in the preparation of 3MBM was not considered here.

There is also the possibility of using metal catalysts on an inorganic support for the reduction, for instance a copper catalyst in the presence of nickel and/or palladium on a silicate (patent: CN1861253). Lu et al. (Zhejiang Gongye Daxue Xuebao (2002), 30(5), 464-466) also reported carbon nanotubes as support material.

Owing to the thermal instability of oNPA (in an about 20% by weight solution of oNPA in a mixture with about 20% by weight of toluene and about 60% by weight of methanol, distinct exothermicity begins at only about 130° C. as a result of the decomposition of the reactant) and to the expected evolution of heat during the reaction, and owing to the observed low conversions of only about 70%, such a reaction regime cannot be performed on the industrial scale.

It was an object of the present invention to provide a process for preparing benzomorpholine derivatives by hydrogenating o-nitrophenoxy carbonyl compounds, in which the hydrogenation of these nitrophenoxy carbonyl compounds is performed at a very low temperature and in the presence of an inexpensive catalyst.

The process according to the invention, which achieves this object, has now been found.

The invention therefore provides a process for preparing benzomorpholine derivatives of the general formula (I)

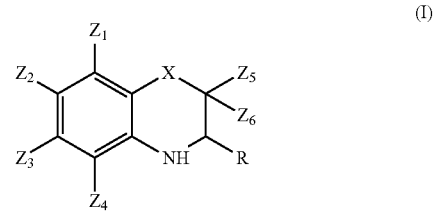

(I)

in which

R can be hydrogen, or a $C_1$-$C_{10}$-alkyl, phenyl or tetrahydrofuryl radical, $Z_1$ to $Z_6$ can each independently be hydrogen or a $C_1$-$C_{10}$-alkyl radical and X can be oxygen or sulphur, by hydrogenating o-nitrophenoxy carbonyl compounds of the general formula (II)

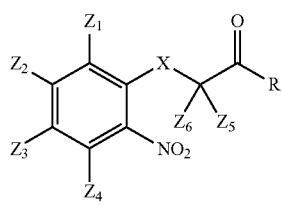

(II)

in which

R, $Z_1$ to $Z_6$ and X are each as defined for formula (I), wherein the hydrogenation of compounds of the general formula (II) is performed with hydrogen gas in the presence of a molybdenum- and/or iron- and/or aluminium-doped sponge metal catalyst based on nickel or cobalt with ring formation.

For the hydrogenation of the o-nitrophenoxy carbonyl compound, it has been found that, surprisingly, this reaction can be performed on the industrial scale in the presence of sponge metal catalysts based on a nickel/molybdenum alloy virtually without significant side reactions (for example to give dimers of 3-methylbenzomorpholine or to give partly hydrogenated or ring-hydrogenated compounds, or to give other, undesired by-products) at low temperatures (30-90° C.) with short residence times (about 1 hour).

Sponge metal catalysts based on undoped cobalt and based on undoped nickel are completely unsuitable for the conversion at low temperatures, whereas a molybdenum-doped nickel catalyst was found to be particularly advantageous and exhibited a result comparable to that with the noble metal catalyst. Preference is given to using a molybdenum-doped catalyst, for example a sponge metal catalyst based on nickel, which, as well as nickel and aluminium, also contains between 0.5 and 3% molybdenum, as obtainable, for example, under the AMPERKAT Ni—Mo 3706 trade name from H. C. Starck (Goslar, Germany). For the preparation of the catalyst, molybdenum must already be present in the pre-alloy. The pre-alloy is melted, then cooled very rapidly by atomizing into water and then leached with sodium hydroxide solution. In addition to the molybdenum-containing catalysts, it is also possible to use iron-containing sponge metal catalysts based on nickel with an iron content of 12-15% by weight iron in the finished catalyst (for example AMPERKAT Ni—Fe 6606 from H. C. Starck (Goslar, Germany), which can be prepared from an iron-containing nickel-aluminium pre-alloy, by atomizing into water). In addition, chromium is also a useful doping element, in particular in combination with iron, nickel and aluminium, and in the form of a slowly solidified pre-alloy which is subsequently comminuted and leached (for example AMPERKAT Ni—FeCr 4546 from H. C. Starck (Goslar, Germany)).

Moreover, the sponge metal catalyst used in the process according to the invention surprisingly exhibits a significantly longer service life than a noble metal catalyst under the selected experimental conditions with >90 g of nitro compound per gram of catalyst (without intermediate washes of the catalyst).

In general, the hydrogenation is performed in a solvent mixture of a $C_1$-$C_3$-alcohol such as methanol, ethanol or isopropanol in a mixture with an aromatic solvent such as toluene, or else exclusively in the corresponding alcohol, provided that the solubility of the oNPa is sufficient at the low temperatures present. The mixing ratios (in parts by weight) are between 1:100 aromatic solvent to alcohol up to 20:100 aromatic solvent to alcohol, such that, even taking account of the water of reaction which forms, monophasicity of the reaction mixture at the end of the reaction preferably (but not necessarily) remains guaranteed. Preference is given to a toluene/methanol mixture as the solvent for the hydrogenation with a mixing ratio of 9.7:100 toluene to methanol. Based on the description from US 2006/0017946 A1, it is, however, also possible to use solvent mixtures with a significantly higher proportion of toluene.

The influence of the "pH" measured in the solvent mixture (the term "pH" could actually be replaced in the present case by a measured voltage against a reference electrode, since measurements were made in a nonaqueous system) has a surprising influence on the formation of secondary components and the service life of the catalyst. A favourable pH has been found to be between 7 and 10, preferably between 8 and 10, more preferably 8-9. Typically, the pH is measured with a commercial glass pH electrode.

The hydrogen pressure during the hydrogenation is typically between 10 and 400 bar, preferably between 200 and 240 bar, more preferably 220 bar.

The reaction temperature in the course of hydrogenation is typically in the range between 30 and 90° C., preferably 60° C.

The hydrogenation can be performed batchwise or preferably continuously. For example, in a continuous procedure, the residence time of the reactant solution may be between 30 and 180 minutes, preferably 60 minutes, and the catalyst space velocity may be in the range from 0.1 to 20 g, preferably 1.5 to 3 g, of nitro compound per gram of catalyst and hour.

Selection of these experimental parameters minimized the number and amount of secondary components. One particularly relevant factor here is the formation of the 3-MBM dimer, which otherwise rises in the event of selection of incorrect reaction conditions and perceptively reduces the yield and purity of 3-MBM.

By the process according to the invention, it is generally possible to prepare benzomorpholine derivatives of the formula (I) specified. This is understood to mean those in which X is an oxygen atom (benzomorpholine derivatives) but also those in which X is a sulphur atom (benzoparathiazine derivatives). X is preferably an oxygen atom.

More preferably, in the process according to the invention, o-nitrophenoxyacetone, which can be prepared, for example, from the reaction of o-nitrophenol with chloroacetone, is hydrogenated to 3,4-dihydro-3-methyl-2H-1,4-benzoxazine (3-MBM) ($Z_1$-$Z_6$=hydrogen, X=oxygen and R=methyl in formula (I)). 3-MBM can be processed further, for example, to give 4-(dichloroacetyl)-3,4-dihydro-3-methyl-2H-1,4-benzoxazine (benoxacor), which is used as a safener in herbicides.

The examples which follow further illustrate the invention, but without restricting its scope.

EXAMPLES

In Examples 1, 2 and 11 described, the starting material was always pure, crystallized o-NPA which was prepared based on the method from US 2006/0017946 A1, and finally by crystallization from an isopropanol-containing solvent mixture.

The following catalysts were used in the examples (all data in % by weight):

Catalyst 1: Amperkat SK Co 3706 from HC Starck, Goslar, formed from atomized and hence rapidly solidified pre-alloy which contains essentially cobalt and aluminium. The catalyst used contains 94-98% cobalt, 1-5% aluminium, not more than 1.5% nickel, not more than 1% iron Catalyst 2: Amperkat SK Ni—Mo 3706 from HC Starck, prepared by leaching an atomized (rapidly solidified) pre-alloy which contains nickel, aluminium and molybdenum. The catalyst used contains 91-96% nickel, 4-7% aluminium, 0.5-3% molybdenum and not more than 1% iron Catalyst 3: Amperkat SK Ni 3706 from HC Starck, Goslar, prepared by leaching an atomized (rapidly solidified) pre-alloy which contains nickel and aluminium. The catalyst used contains 93-96% nickel, 3-7% aluminium and not more than 1% iron Catalyst 4: Amperkat SK Ni—Fe 6606 from HC Starck, Goslar, prepared by leaching an atomized (rapidly solidified) pre-alloy which contains nickel, iron and aluminium. The catalyst used contains 77-82% nickel, 4-7% aluminium and 12-15% iron Catalyst 5: Amperkat SK Ni—FeCr 4546 from HC Starck, Goslar, prepared by leaching a pre-alloy (slowly solidified) in bars, which contains nickel, iron, chromium and aluminium. The catalyst used contains 82-90% nickel, 6-10% aluminium, 2-5% chromium and 2-5% iron Catalyst 6: K-0126 10% Pt metal on activated carbon from Heraeus, Hanau (comparative)

Catalyst 7: K-8610 1% Pt metal on carbon from Heraeus, Hanau (comparative)

Catalyst 8: 5% Pd metal on activated carbon (comparative)

Catalyst 9: prepared from a pre-alloy according to the method from patent application DE 197 53501 A1, Example 3, and leached in sodium hydroxide solution.

The figures for the 3MBM contents are percentages by weight, which were obtained from calibrated GC measurements. In spite of this, these figures are afflicted with uncertainties, such that measurements slightly higher than 100% can also arise. The content of 3MBM dimers reported was not calibrated (the measurements reported are area percentages of the GC method), and so these figures can be understood only as a guideline and in a relative comparison.

Example 1

Comparison of various sponge metal catalysts and of a noble metal catalyst in the hydrogenation of o-nitrophenoxy-acetone to 3MBM in isopropanol/toluene at 60° C./hydrogen pressure 100 bar In six identical high-pressure reactors, in each case 1.3 g of o-nitrophenoxyacetone (with virtually 100% purity according to GC analysis), 1.7 g of isopropanol (for analysis) and 6.9 g of toluene were weighed in together with 0.6 g of catalyst (based on the dry weight).

A hydrogen pressure of 100 bar was set, and the temperature was increased to 40° C. and left under these conditions for 30 minutes. The pressure in the reactors was then lowered to ambient pressure and the reaction product was analysed by GC analysis.

| Catalyst | 3MBM content (% by wt.) | oNPA content (% by wt.) | Number of secondary components | Total secondary components (area %) |
|---|---|---|---|---|
| 1 | 0 | 7.0 | 3 | 1.5 |
| 2 | 9.1 | 0 | 1 | 1.7 |
| 3 | 1.4 | 0 | 2 | 0.9 |
| 4 | 2.8 | 0 | 1 | 2.5 |
| 5 | 7.2 | 0 | 1 | 2.8 |
| 6 (comparative) | 8.7 | 0 | 0 | 0 |

Example 2

Comparison of various sponge metal catalysts and of a noble metal catalyst in the hydrogenation of o-nitrophenoxy-acetone to 3MBM in isopropanol/toluene at 85° C./hydrogen pressure 200 Bar In six identical high-pressure reactors, in each case 8 g of a 16.4% by weight o-nitrophenoxyacetone solution (dissolved in a mixture 55.6% by weight of methanol and 28% by weight of toluene) were weighed in, together with 0.6 g of catalyst (based on the dry weight).

A hydrogen pressure of 200 bar was established and the temperature was increased to 85° C. and left under these conditions for 15 minutes. The pressure in the reactors was then lowered to ambient pressure and the reaction product was analysed by GC analysis.

| Catalyst | 3MBM content (% by wt.) | oNPA content (% by wt.) | Number of secondary components | Total secondary components (area %) |
|---|---|---|---|---|
| 5 | 6.5 | 0.1 | 12 | 3.4 |
| 7 | 9.2 | 0 | 8 | 2.4 |
| 1 | 9.6 | 0 | 8 | 1.6 |
| 4 | 8.8 | 0.2 | 8 | 2.1 |
| 8 (comparative) | 9.5 | 0 | 9 | 3.0 |
| 9 | 7.4 | 0.2 | 11 | 2.4 |

Example 3

Continuous hydrogenation of a 20.6% by weight o-NPA solution with the aid of a high-pressure autoclave (with overflow) at 150 bar of hydrogen using catalyst 2 at temperatures between 70-85° C.

A stainless steel autoclave which had been attached to an overflow with a frit (such that the internal volume available to liquids was limited to about 455 ml) was initially charged with 15 g of catalyst 2 (calculated as dried material) in 200 g of methanol. An about 20% by weight o-NPA solution (with 20% by weight of toluene and 60% by weight of methanol, prepared by the process described in US 2006/0017946 A1 without further purification) was metered into this stirred suspension under a hydrogen pressure of 150 bar, such that the initial mean residence time of the solution was about 60 minutes. In the course of the experiment, the temperature was increased and the residence time was prolonged. Samples were taken and analysed at time intervals of 1 to 2 hours.

The yield of 3MBM was almost always significantly below the economically necessary 90% for all experimental parameters (see FIG. 1: diagram for Example 3); the content of secondary components was comparatively high. Nevertheless, the catalyst can be used as a hydrogenation catalyst in a continuous process under these conditions, and a conversion of 66 g of o-nitrophenoxyacetone per gram of catalyst was achieved. The total conversion to 3MBM was 78%, and 11% 3MBM dimer based on the 3MBM formed was determined.

Example 4

Continuous hydrogenation of a 14.8% by weight o-NPA solution with the aid of a high-pressure autoclave (with overflow) at 200 bar of hydrogen using catalyst 2 at a temperature of 85° C.

An experimental setup as described under Example 3 was initially charged with 45 g of catalyst 2 (calculated as dried material) in 200 g of methanol. The oNPA solution from Example 3 (diluted with methanol to a concentration of about 14.8% by weight of o-NPA) was metered into this stirred suspension under a pressure of 200 bar of hydrogen, such that the mean residence time was about 1 hour. At intervals of one to two hours, samples were taken and analysed by GC analysis; see figure for results.

The analytical yield of 3MBM was almost always close to the theoretical yield over the experimental period. The content of 3-MBM dimer, however, was quite high at 5% based on the 3MBM. The yield of 3MBM measured in the overall sample was more than 90%.

Nevertheless, the catalyst can be used as a hydrogenation catalyst in a continuous process under these conditions. In the present experiment, a conversion of 40 g of o-nitrophenoxyacetone per gram of catalyst was achieved.

Example 5

Continuous hydrogenation of a 16.2% by weight o-NPA solution with the aid of a high-pressure autoclave (with overflow) at 200 bar of hydrogen using catalyst 5 at a temperature of 85° C.

An experimental setup as described under Example 3 was initially charged with 27 g of catalyst 5 (calculated as dried material) in 200 g of methanol. The o-NPA solution from Example 3 (diluted with methanol to a content of 16.2% by weight) was metered into this stirred suspension under a pressure of 200 bar of hydrogen sufficiently rapidly that the mean residence time was about one hour.

The yield of 3MBM measured in the overall sample was 81% based on the o-nitrophenoxyacetone used. The content of 3-MBM dimer, however, was too high at around 10% based on the 3MBM. Nevertheless, the catalyst can be used as a hydrogenation catalyst in a continuous process under these conditions. In the present experiment, a conversion of 30 g of o-nitrophenoxyacetone per gram of catalyst was achieved.

Example 6

Continuous hydrogenation of a 16.5% by weight o-NPA solution with the aid of a high-pressure autoclave (with overflow) at 200 bar of hydrogen using catalyst 5 at a temperature of 85° C.

An experimental setup as described under Example 3 was initially charged with 40 g of catalyst 5 (calculated as dried material) in 200 g of methanol. The o-NPA solution from Example 3 (diluted with methanol to a content of 16.5% by weight) was metered into this stirred suspension under a pressure of 200 bar of hydrogen sufficiently rapidly that the mean residence time was 40 minutes.

The yield of 3MBM measured in the overall sample was 97% based on the o-nitrophenoxyacetone used. The content of 3-MBM dimer, however, was too high at around 3.6% based on the 3MBM.

Nevertheless, the catalyst can be used as a hydrogenation catalyst in a continuous process under these conditions. In the present experiment, a conversion of 12 g of o-nitrophenoxyacetone per gram of catalyst was achieved.

Example 7

Continuous hydrogenation of a 16.5% by weight o-NPA solution with the aid of a high-pressure autoclave (with overflow) at 200 bar of hydrogen using catalyst 5 at a temperature of 60° C.

An experimental setup as described under Example 3 was initially charged with 27 g of catalyst 5 (calculated as dried material) in 200 g of methanol. The o-NPA solution from Example 3 (diluted with methanol to a content of 16.5% by weight) was metered into this stirred suspension under a pressure of 200 bar of hydrogen sufficiently rapidly that the mean residence time was 55 minutes.

The yield of 3MBM measured in the overall sample was 82% based on the o-nitrophenoxyacetone used. The content of 3-MBM dimer, however, was too high at around 3.3% based on the 3MBM.

Nevertheless, the catalyst can be used as a hydrogenation catalyst in a continuous process under these conditions. In the present experiment, a conversion of 36 g of o-nitrophenoxyacetone per gram of catalyst was achieved.

Example 8

Continuous hydrogenation of a 16.4% by weight o-NPA solution with the aid of a high-pressure autoclave (with overflow) at 220 bar of hydrogen using catalyst 2 at a temperature of 60° C.

An experimental setup as described under Example 3 was initially charged with 25 g of catalyst 2 (calculated as dried material) in 200 g of methanol. The o-NPA solution from Example 3 (diluted with methanol to a content of 16.4% by weight) was metered into this stirred suspension under a pressure of 220 bar of hydrogen sufficiently rapidly that the mean residence time was 66 minutes.

The yield of 3MBM measured in the overall sample was 74% based on the o-nitrophenoxyacetone used. 3-MBM dimer was undetectable in the samples.

Nevertheless, the catalyst can be used as a hydrogenation catalyst in a continuous process under these conditions. In the present experiment, a conversion of more than 40 g of o-nitrophenoxyacetone per gram of catalyst was achieved.

Example 9

Continuous hydrogenation of a 16.4% by weight o-NPA solution with the aid of a high-pressure autoclave (with overflow) at 220 bar of hydrogen using catalyst 2 at a temperature of 70° C.

An experimental setup as described under Example 3 was initially charged with 25 g of catalyst 2 (calculated as dried material) in 200 g of methanol. The o-NPA solution from Example 3 (diluted with methanol to a content of 16.4% by weight) was metered into this stirred suspension under a pressure of 220 bar of hydrogen sufficiently rapidly that the mean residence time was 66 minutes.

The yield of 3MBM measured in the overall sample was 96% based on the o-nitrophenoxyacetone used. However, 3.3% 3-MBM dimer was detected based on the 3MBM formed.

Nevertheless, the catalyst can be used as a hydrogenation catalyst in a continuous process under these conditions. In the present experiment, a conversion of approximately 40 g of o-nitrophenoxyacetone per gram of catalyst was achieved.

Example 10

Continuous hydrogenation of a 16.4% by weight o-NPA solution with the aid of a high-pressure autoclave (with overflow) at 220 bar of hydrogen using catalyst 2 at a temperature of 60° C.

An experimental setup as described under Example 3 was initially charged with 25 g of catalyst 2 (calculated as dried material) in 200 g of methanol. The o-NPA solution from Example 3 (diluted with methanol to a content of 16.4% by weight and adjusted to a pH of 8 with NaOH) was metered into this stirred suspension under a pressure of 220 bar of hydrogen sufficiently rapidly that the mean residence time was 66 minutes.

The yield of 3MBM measured in the overall sample was more than 90% based on the o-nitrophenoxyacetone used. However, 3.1% 3-MBM dimer based on the 3MBM formed was detected. The individual values are plotted in the figure.

Nevertheless, the catalyst can be used as a hydrogenation catalyst in a continuous process under these conditions. In the present experiment, a conversion of 62 g of o-nitrophenoxyacetone per gram of catalyst was achieved.

Example 11

Continuous hydrogenation of a 17.5% by weight o-NPA solution with the aid of a high-pressure autoclave (with overflow) at 220 bar of hydrogen using catalyst 2 at a temperature of 60° C.

An experimental setup as described under Example 3, except in a autoclave with a volume of 900 ml, was initially charged with 50 g of catalyst 2 (calculated as dried material) in 900 ml of methanol. A 17.5% by weight oNPA solution (prepared from crystallized oNPA with a content of >99% by weight and 6.7% by weight of toluene and 75.7% by weight of methanol, and stored at 40° C. and adjusted to a pH between 8 and 9 with NaOH) was metered into this stirred suspension under a pressure of 220 bar of hydrogen sufficiently rapidly that the mean residence time was about 60 minutes.

The yield of 3MBM measured in the overall sample was virtually quantitative. Secondary components formed were on the detection limit. For details see figure.

In the present experiment, a conversion of 92 g of o-nitrophenoxyacetone per gram of catalyst was achieved.

This example was reproduced in five experiments.

What is claimed is:

1. Process for preparing benzomorpholine derivatives of the general formula (I)

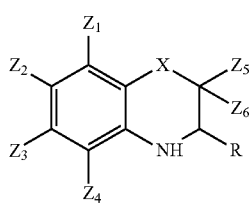

(I)

in which

R is hydrogen, or a $C_1$-$C_{10}$-alkyl, phenyl or tetrahydrofurfuryl radical, $Z_1$ to $Z_6$ are each independently hydrogen or a $C_1$-$C_{10}$-alkyl radical and X is oxygen or sulphur, by hydrogenating o-nitrophenoxy carbonyl compounds of the general formula (II)

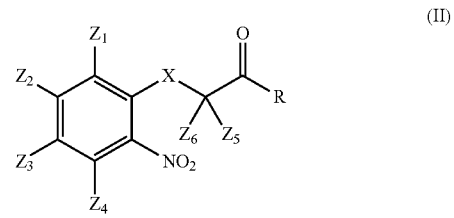

(II)

in which

R, $Z_1$ to $Z_6$ and X are each as defined for formula (I), wherein the hydrogenation of compounds of the general formula (II) is performed with hydrogen gas in the presence a catalyst selected from the group consisting of a molybdenum-, iron-, aluminium-, chromium-doped sponge metal catalyst based on nickel or cobalt and wherein the pH during the hydrogenation is set to a value between 8 and 10.

2. Process according to claim 1, wherein the o-nitrophenoxy carbonyl compound of the general formula (II) has been purified by recrystallization before the hydrogenation.

3. Process according to claim 1, wherein the pressure of the hydrogen gas is in the range between 10 and 400 bar.

4. Process according to claim 1, wherein the temperature during the hydrogenation is in the range between 40 and 90° C.

5. Process according to claim 1, wherein the hydrogenation is performed continuously with a mean residence time of the reactant solution in the catalyst suspension between 30 and 180 minutes, and a catalyst space velocity of 0.1 to 20 g of nitro compound per gram of catalyst and hour.

6. Process according to claim 1, wherein the hydrogenation is performed in a solvent mixture of a $C_1$-$C_3$-alcohol and an aromatic solvent.

7. Process according to claim 1, wherein the sponge metal catalyst is a sponge metal catalyst based on nickel with 0-15% by weight of iron.

8. Process according to claim 1, wherein the sponge metal catalyst is a sponge metal catalyst based on nickel with 0-4% by weight of molybdenum.

9. Process according to claim 1, wherein the sponge metal catalyst is a sponge metal catalyst based on cobalt with 0-5% by weight of aluminium.

10. Process according to claim 1, wherein the pH during the hydrogenation is set to a value between 8 and 9.

* * * * *